US008573834B2

(12) United States Patent
Bik

(10) Patent No.: US 8,573,834 B2
(45) Date of Patent: Nov. 5, 2013

(54) CONNECTIONLESS COOLING SYSTEM

(75) Inventor: Tadeusz Bik, North Vancouver (CA)

(73) Assignee: Honeywell ASCa Inc., Mississauga (CA)

( * ) Notice: Subject to any disclaimer, the term of this patent is extended or adjusted under 35 U.S.C. 154(b) by 361 days.

(21) Appl. No.: 13/107,877

(22) Filed: May 14, 2011

(65) Prior Publication Data
US 2012/0285235 A1 Nov. 15, 2012

(51) Int. Cl.
*G01N 25/00* (2006.01)
(52) U.S. Cl.
USPC .......................................................... 374/10
(58) Field of Classification Search
None
See application file for complete search history.

(56) References Cited

U.S. PATENT DOCUMENTS

| | | |
|---|---|---|
| 5,299,249 A | 3/1994 | Burke |
| 5,654,799 A | 8/1997 | Chase |
| 5,793,486 A | 8/1998 | Gordon |
| 6,511,224 B1 | 1/2003 | Lu |
| 6,909,283 B2 | 6/2005 | Emeric |
| 7,494,567 B2 | 2/2009 | Haran |
| 7,532,115 B2 | 5/2009 | Neill |
| 7,599,427 B2 | 10/2009 | Bik |
| 7,637,315 B2 | 12/2009 | Ichinose |

*Primary Examiner* — Lisa Caputo
*Assistant Examiner* — Brandi N Hopkins
(74) *Attorney, Agent, or Firm* — Cascio Schmoyer & Zervas

(57) ABSTRACT

Mobile devices are re-supplied with fluids on a periodic basis thereby eliminating the need to maintain a permanent connection between an external fluid supply and the moving device. Electronic scanning devices generate heat and operate at varying and high temperature conditions that interfere with operations of the scanner heads. Circulating a heat transfer fluid through the sensor head removes excess heat from heat sensitive regions of the sensor head during operations. Once the heat transfer fluid reaches a predetermined temperature or after passage of a predetermined length of time, the scanner head is maneuvered to a docking station where it is coupled to an external heat fluid source where fresh fluid is supplied to the scanner head.

16 Claims, 2 Drawing Sheets

CONNECTIONLESS COOLING SYSTEM

FIELD OF THE INVENTION

The present invention generally relates to techniques for replenishing fluids in a moving apparatus and more particularly to methods for controlling the temperature of industrial sensor scanner measurement systems for determining parameters of continuous sheet materials during production. The temperature of the sensor head is regulated by circulating a heat transfer medium that is replenished periodically from an external stationary coolant-recharging source that is not permanently connected to the circulating medium.

BACKGROUND OF THE INVENTION

Various sensor systems have been developed for detecting sheet properties "on-line," i.e., on a sheet-making machine while it is operating. Sensors for continuous flat sheet production processes typically employ single or dual-sided packages with on-line sensors that traverse or scan traveling webs of sheet material during manufacture. With dual scanners, the heads or assemblies are fixed to beams that span both sides of the sheet with linear guidance tracks to allow the sensors to move in unison in the cross direction, i.e., in the direction perpendicular to the direction of sheet travel. Depending upon the sheet-making operation, cross-directional distances can range up to about twelve meters or more. In the paper making art, for instance, the on-line sensors detect variables such as basis weight, moisture content, and caliper of sheets during manufacture.

The electronics in the enclosed scanner heads generate heat that must be dissipated. In addition, paper and continuous web scanners are often operated at varying and high temperature conditions. Thermal loading originate from a myriad of sources in the proximity of the scanner that cause ambient air temperature gradients between the beams that are positioned above and below the sheet of paper. Major contributors include hot or cold air sources, such as exterior doors, openings to cold basements, and hot drier exits, and directional heating from infrared radiation sources typically used to dry coatings on sheets. The temperature fluctuations adversely affect the sensors. Current scanners have external coolant sources that continuously supply circulating coolant to internal cooling channels within the scanner heads. These external coolant sources however are permanently connected to the scanner heads as the latter travels back and forth during operations. The associated connections add to the complexity and costs of the scanning systems and adversely affect the measurement accuracy of the scanners.

SUMMARY OF THE INVENTION

The present invention is based, in part, on the recognition that the intricate and bulky machinery that is required to continuously supply scanning heads and other mobile devices with heat transfer medium can be eliminated with a simpler design where the medium in the mobile device is replenished only on an as needed basis. In this fashion, a scanner head, for instance, which has an internal coolant circulating system, is still able to minimize temperature-induced distortions on sensor measurements even though it is not connected to an external coolant source during operations of the scanner.

In one aspect, the invention is directed to a connectionless fluid replenishing system that includes:
a mobile device having a fluid that is circulated within fluid channels in the mobile device: and
an external fluid recharging source that includes means for coupling the external fluid recharging source to the mobile device to recharge the fluid channels with fresh fluid, which can be a liquid or gas, on an intermittent basis, characterized in that the external fluid recharging source is decoupled from the mobile device during operation of mobile device.

In another aspect, the invention is directed to a system for measuring properties of the composition of traveling webs of sheet material during manufacture, which includes:
a track means mounted to extend generally parallel to one lace of a traveling web in the cross direction;
a sensor device that is supported in a housing that is mounted on the track means and that moves along the cross direction, wherein the housing includes a coolant reservoir that circulates coolant through a heat exchanger that is in thermal communication with the sensor device; and
an external coolant recharging source that includes means for coupling the coolant source to the coolant reservoir to recharge the coolant reservoir with fresh coolant and characterized in that the coolant recharging source is not connected to the coolant reservoir when the sensor device is in motion.

In a further aspect, the invention is directed to a method of regulating the temperature of a mobile heat sensitive apparatus that includes the steps of:
(a) providing a fluid reservoir:
(b) circulating fluid from the fluid reservoir through a heat exchanger that is in thermal contact with the heat sensitive apparatus as the heat sensitive apparatus is in motion;
(c) providing a stationary external fluid recharging source; and
(d) replacing fluid in the fluid reservoir with fresh fluid from the external fluid recharging source at intermittent intervals with the proviso that the fluid reservoir is not permanently connected to the external fluid recharging source.

DESCRIPTION PREFERRED EMBODIMENTS

The present invention can be implemented in any system that employs a mobile device in which a liquid or gas is replenished periodically. The term "mobile device" refers to an apparatus that typically moves along a fixed path of motion, which can be defined by a frame, track, a guide or a rail. The mobile device can move in any direction along the path of motion. The apparatus is not connected to an external source of fluid transfer medium as it moves along the fixed path.

The mobile device can be one that generates excessive internal heat or that is operated in an environment at elevated temperatures so that the fluid heat transfer medium serves as a coolant. Conversely, the mobile device can be one that is operated in a cold environment so that the fluid serves as a source of heat to prevent the temperature of the device from falling below a critical limit. In both heat control systems, the temperature of the mobile device is preferably modulated passively, that is, the mobile device does not include any internal energy source that cools or heats the heat transfer medium as it circulates through the mobile device. The invention obviates the need for an external coolant source to be permanently and continuously connected via extended, bulky supply lines to the scanning sensor.

While the invention will be illustrated as part of a sensor system for measuring physical properties of a moving web, it is understood that the can be implemented in any system where fluid within a mobile device must be replenished. For example, it is contemplated that for fluid dispensing systems such as liquid ink jet scanning printers that employ ink cartridges or similar ink storage devices, that the inventive technique can be used so that ink is replaced periodically as it becomes depleted. This obviates the need to replace the entire cartridge or to use ink supply lines.

Figure 1:
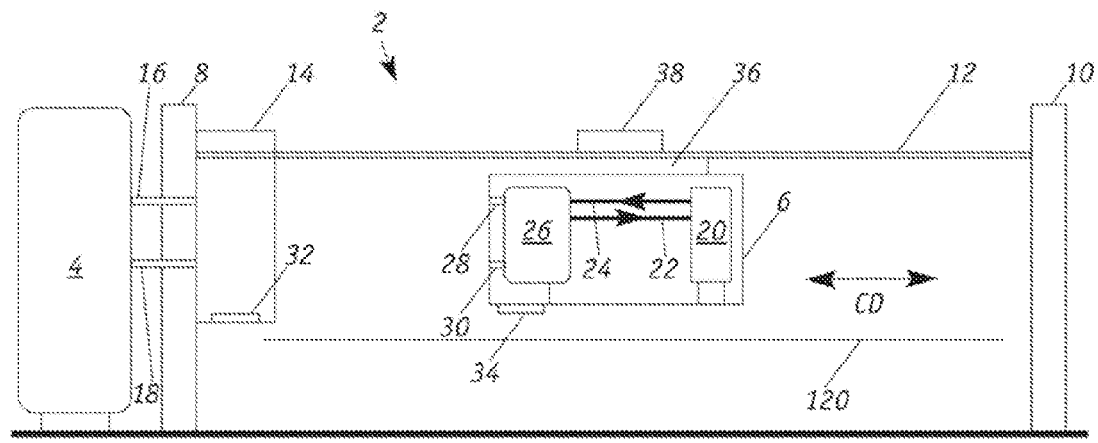
FIGS. 1 and 2 illustrate a scanner system employing a moving sensor head and an external heat transfer fluid source, shown in the scanning and charging modes, respectively.

FIG. 1 shows a scanning system 2 with scanner sensor head 6 that is supported by an upper support beam 12 that is mounted onto a pair of upright end members 8, 10. Scanner head 6 is mounted on a roller carriage 36 which engages a track on beam 12 as the carriage advances along the cross direction (CD) to a moving sheet 120, which is traveling in the machine direction which is transverse to the CD. A drive mechanism 38 moves roller carriage 36.

Figure 2:
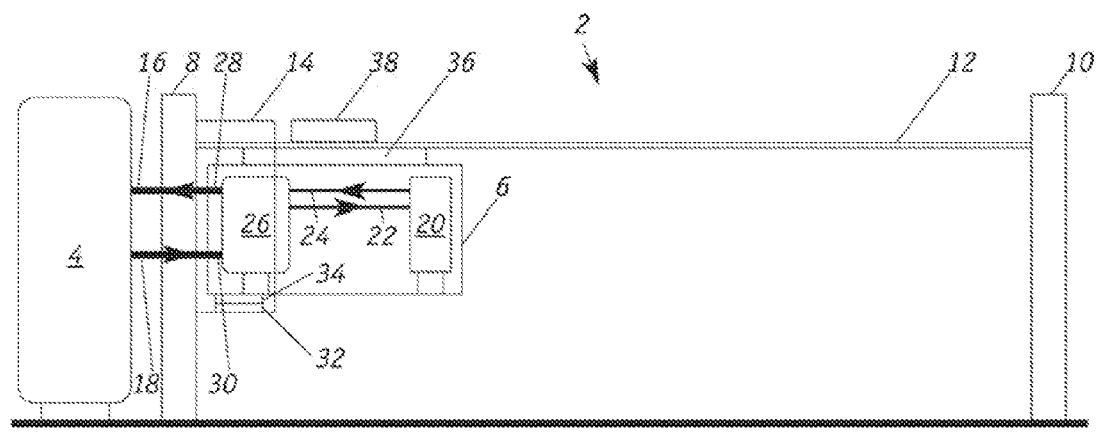

Scanner head 6 is equipped with an internal heat exchanger 20 that is supplied with a coolant reservoir 26 that contains a heat transfer medium such as a mixture of glycol and water. Heat exchanger 20 is configured and positioned within scanner head to serve as a heat sink to remove from at least the heat sensitive regions of sensor head 6. During operations of the scanning system, wherein scanner head 6 moves back-and-forth over a web product 120 being monitored, coolant is circulated between a coolant reservoir 26 and heat exchanger 20 via lines 22, 24. An external supply 4 of heat transfer medium, which is positioned remotely from scanning system 2, includes coupling mechanisms 16, 18 configured to engage corresponding devices 28, 30, respectively during the recharging phase of operation. A docking station 14 that is equipped with guide rail 32 that engages bearings 34 on sensor head 6 as it maneuvers into position as shown in FIG. 2. A conventional drive mechanism 38 drives scanner head 6 back and forth along beam 12.

During the recharging phase as shown in FIG. 2, fresh colder coolant from external coolant source 4 is exchanged for warmer coolant from coolant reservoir 26. Lines 22, 24 between coolant reservoir 26 and heat exchanger 20 remain open to allow warmer coolant within heat exchanger 20 to be removed as well.

Figure 3:
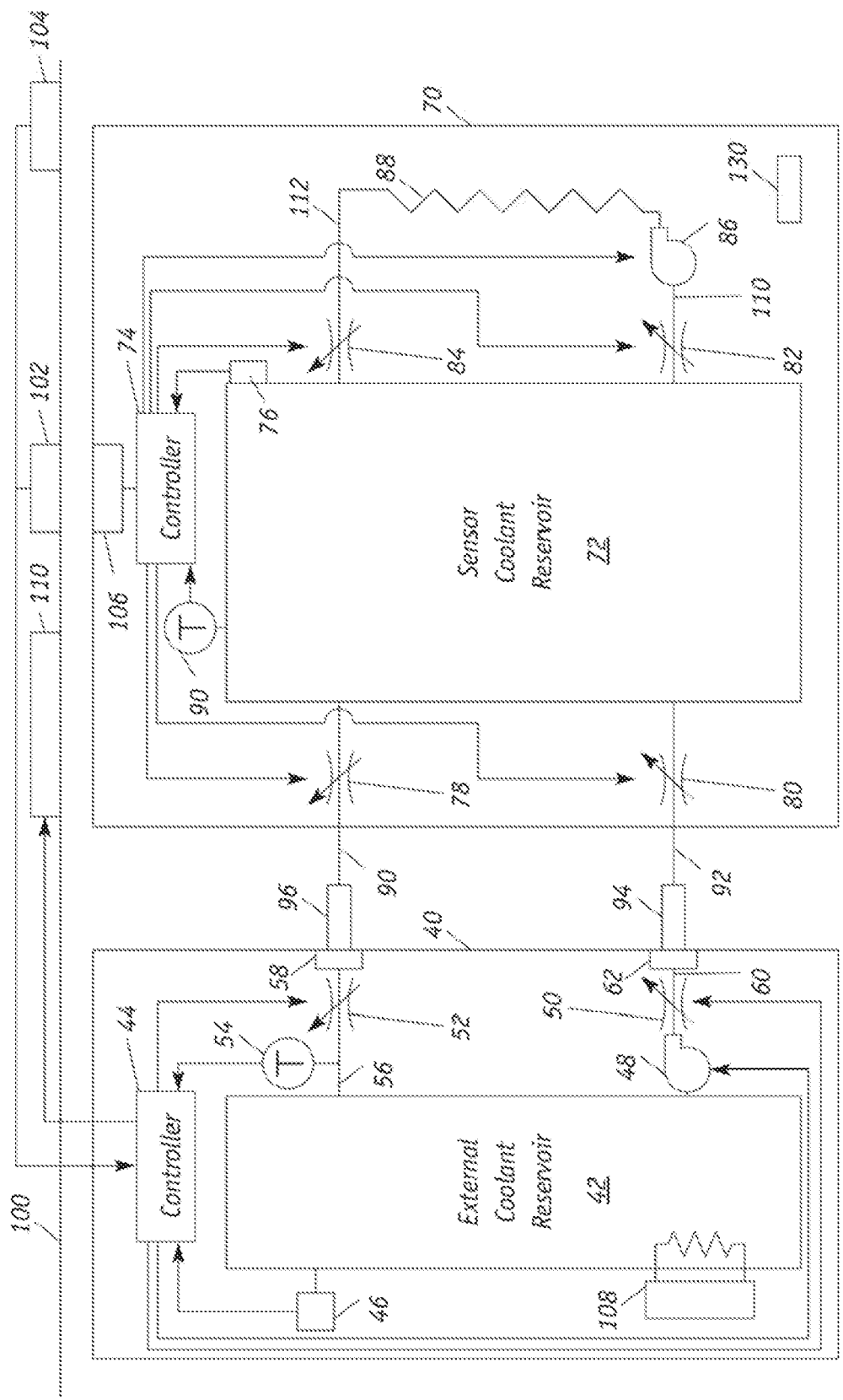
FIG. 3 illustrates the external coolant source, sensor coolant reservoir and connections between these units.

FIG. 3 depicts the control mechanism, which operates the connectionless fluid replenishing system that includes an external coolant compartment 40 that houses an external coolant source 42 and scanner head 70 that houses sensor coolant reservoir 72. External coolant source 42 has an outlet line 60 that includes a pump 48 and valve 50 and an inlet line 56 that includes valve 52 and temperature gauge 54. The amount of coolant within external coolant source 42 is monitored with fluid level gauge 46. Outlet and inlet lines 60, 56 have female connectors 58, 62 at their respective distal ends. A refrigeration unit such as heat pump 108 can be employed to cool the fluid within external coolant source 42. A controller 44 receives signals from temperature gauge 54 and level gauge 46 and regulates heat pump 108, pump 48, and valves 50, 52.

Sensor coolant reservoir 72 is connected to a heat exchanger 88 through lines 110, 112 that include valves 32, 84 and pump 86. It is also equipped with an outlet line 90 includes with valve 78 and a male connector 96 and an inlet line 92 that includes valve 80 and a male connector 94. Heat exchanger 88 is positioned in the vicinity and in thermal contact with heat generating sensor apparatus 130. The temperature of the coolant within sensor coolant reservoir 72 is measured with temperature gauge 90 and the amount of coolant therein is measured with level gauge 76. Controller 74 receives signals from temperature and level gauges 90, 74 and regulates valves 78, 80, 82 and 84 and pump 86.

The temperature and other parameters of the coolant within sensor coolant reservoir 72 can be transmitted to an operator via a standard wireless antenna or a micro range radio frequency communications link can be employed. As shown in FIG. 3, scanner head 70 includes a transmitter 106 that is a micro range transmitter capable of transmitting data only over a very short distance. A plurality of receivers 102, 104 are positioned or distributed on beam 100 along the path of motion scanner head 70. Receiver 104 is positioned away from stationary coolant storage compartment 40 whereas receiver 102 is positioned so that it is aligned with transmitter 106 during the recharging phase as described herein. The receivers 102, 104 act as an access point for data transmission. As scanner head 70 moves along a fixed path that is parallel to beam 100, transmitter 106 will align with one of receivers 102, 104, to establish an RF data transfer point 125 is formed. Micro range RF communication links are described in U.S. Pat. No. 7,599,427 to Bik, which is incorporated herein by reference.

During operation of scanner head 6 as shown in FIG. 1 wherein the head travels back and forth along beam 12, coolant is circulated between coolant reservoir 26 and heat exchanger 20 to remove some of the heat that is generated by the electronics of the scanner as well as heat that is derived from the environment. At the start of operations of scanner head 6 after being recharged with fresh coolant, the temperature of the coolant in reservoir 26 is at its lowest point. As the coolant is circulated, its temperature rises over time. One technique of maintaining a more constant heat transfer rate is to increase the flow rate of coolant through heat exchanger 88 (FIG. 3) with time. In addition, the flow rate can be adjusted in response to fluctuations in the environmental temperatures as well.

Sensor head 6 does not require an internal device, such as a refrigeration unit, to actively cool the coolant during operation of the mobile scanner head. Instead, the coolant is circulated between coolant reservoir 26 and heat exchanger 20 until a predetermined parameter is reached at which time the coolant is replaced. For example, coolant can be replaced at specific time intervals operations of scanner head 6; alternatively, coolant can be replaced when the coolant temperature reaches a preset limit. One method of implementing the latter scenario is to program scanner head 70 to stop at a position where receiver 104 is aligned with transmitter 106 so that signals that indicative of the coolant temperature are transmitted controller 44. When the coolant reaches a preset temperature, controller activates drive mechanism 110 to transport scanner head 70 toward the docking station so that the connected are coupled as shown in FIG. 3 at which time the recharging phase commences. Once coolant was been replenished, the connectors are disengaged and scanner head 70 resumes operations.

Scanner head 6 can serve as a platform for carrying sensors to detect sheet properties, such as basis weight, in the case of paper. Scanning systems often employ dual scanner heads comprising upper and lower heads that are supported by upper and lower beams or tracks, respectively. Exemplary scanning dual head sensors employing radiation source and detectors are described, for example, in U.S. Pat. No. 5,654,799 to Chase et al., U.S. Pat. No. 5,793,486 to Gordon et al., and U.S. Pat. No. 7,494,567 to Haran, which are incorporated herein by reference. Movement of the dual sensor heads is synchronized so that the heads face the moving sheet and are aligned. For example, a lower head can carry a radiation source, such as a nuclear beta radian source, and upper scanner head may carry a detector. In this case, the sensors can be employed to make basis weight measurements by measuring the radiation intensity incident on the detector when a sheet is present as compared to the beta radiation that is incident upon the detector, when no sheet is present; that is, the basis weight is measured by the beta radiation attenuated by the sheet material. Alternatively, to measure the moisture content of paper, an infrared radiation source can be positioned in the lower scanner head and the radiation that is transmitted through the paper is captured by a detector that is located in the upper scanner head. Analysis of the transmitted radiation yields the moisture content.

The foregoing has described the principles, preferred embodiments and modes of operation of the present invention. However, the invention should not be construed as being limited to the particular embodiments discussed. Thus, the above-described embodiments should be regarded as illustrative rather than as restrictive, and it should be appreciated that variations can be made in those embodiments by workers skilled in the art without departing from the scope of the present invention as defined by the following claims.

What is claimed is:

1. A connectionless fluid replenishing system that comprises:
   a mobile device having a fluid that is circulated within fluid channels in the mobile device; and
   an external fluid-recharging source that includes means for coupling the external fluid recharging source to the mobile device to recharge the fluid channels with fresh fluid on an intermittent basis, characterized in that the external fluid recharging source is decoupled from the mobile device during operation of mobile device.

2. The system of claim 1 wherein the mobile device does not include an active cooling or heating device for the fluid.

3. The system of claim 1 that comprises:
   a housing enclosing a heat generating apparatus, wherein the housing is adapted to be mobile during operation of the mobile device;
   a coolant reservoir supported by the housing that circulates coolant through a heat exchanger that is in thermal contact with the apparatus; and
   a stationary external coolant recharging source that includes means for coupling the coolant recharging source to the coolant reservoir to recharge the coolant reservoir with fresh coolant on an intermittent basis, characterized in that the coolant recharging source is decoupled from the coolant source during operation of the mobile device.

4. The system of claim 3 comprising a drive mechanism adapted to maneuver the housing and a controller configured to activate the drive mechanism to couple the coolant-recharging source to the coolant reservoir.

5. The system of claim 4 wherein the controller is responsive to temperature signals indicative of the temperature of circulating coolant to activate the drive mechanism.

6. The system of claim 4 wherein the controller is configured to activate the drive mechanism at preset time intervals.

7. The system of claim 1 wherein the mobile device moves along a fixed path.

8. The system of claim 1 comprising a docking station that is equipped with guide rail configured to engage corresponding bearings on the housing.

9. The system of claim 1 wherein the mobile device comprises a sensor device that is supported in a housing that is mounted on a first track and wherein the housing includes a coolant reservoir that circulates coolant through a heat exchanger that is in thermal communication with the sensor device.

10. The system of claim 9 wherein the external fluid-recharging source comprises an external cooling recharging source and characterized in that the coolant recharging source is not connected to the coolant reservoir when the sensor device is in motion.

11. The system of claim 9 comprising a drive mechanism adapted to maneuver the housing and a controller configured to activate the drive mechanism to couple the coolant-recharging source to the coolant reservoir.

12. The system of claim 11 wherein the controller is responsive to temperature signals indicative of the temperature of circulating coolant to activate the drive mechanism.

13. The system of claim 11 wherein the controller is configured to activate the drive mechanism at preset time intervals.

14. The system of claim 9 wherein the housing does not include a heat exchanger for cooling the circulating, coolant.

15. The system of claim 9 comprising:
   a second track mounted to extend parallel to the first track such that the first track is vertically spaced apart from the second track; and
   a second sensor device that is supported in a second housing that is mounted on the second track wherein the second housing includes a second coolant reservoir that circulates a second coolant through a second heat exchanger that is in thermal communication with the second sensor device, wherein the first and second sensor devices are aligned as they move back and forth along a cross direction and wherein the first and second sensors define a gap dimensioned to accommodate a web between the gap.

16. The system of claim 15 wherein the first sensor device includes a radiation source that directs radiation onto the face of the web and wherein the second sensor device includes radiation detector that detects radiation transmitted through the web and the radiation source moves back and forth along a cross direction of the web in registration with the radiation detector.

* * * * *